United States Patent
Masaki (10) Patent No.: US 8,944,595 B2
(45) Date of Patent: Feb. 3, 2015

(54) OPHTHALMOLOGIC APPARATUS

(75) Inventor: Toshifumi Masaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/558,226

(22) Filed: Jul. 25, 2012

(65) Prior Publication Data

US 2013/0027663 A1    Jan. 31, 2013

(30) Foreign Application Priority Data

Jul. 29, 2011  (JP) ................................. 2011-167051

(51) Int. Cl.
*A61B 3/14* (2006.01)

(52) U.S. Cl.
CPC ...................................... *A61B 3/14* (2013.01)
USPC ............................ 351/206; 351/205; 351/210

(58) Field of Classification Search
USPC .................... 351/201–204, 215–218
See application file for complete search history.

(56) References Cited

U.S. PATENT DOCUMENTS 4,786,162 A * 11/1988 Fujiwara et al. .............. 351/206

FOREIGN PATENT DOCUMENTS

| CN | 1606398 A | 4/2005 | |
|---|---|---|---|
| CN | 1705236 A | 12/2005 | |
| CN | 1934430 A | 3/2007 | |
| JP | 60-190930 A | 9/1985 | |
| JP | 60190930 * | 9/1985 | ............... A61B 3/14 |

* cited by examiner

*Primary Examiner* — Ricky Mack
*Assistant Examiner* — William Alexander
(74) *Attorney, Agent, or Firm* — Canon USA, Inc. IP Division (57) ABSTRACT

An ophthalmologic apparatus includes an integration unit which integrates a light emission amount of a light source illuminating an target eye, an integral capacitance changing unit which changes a value of an integral capacitance of the integration unit according to the light emission amount necessary for imaging the target eye, a comparison unit which compares a reference value with an integration value integrated by the integration unit using the value of the integral capacitance changed by the integral capacitance changing unit, and a light emission control unit which stops the light emission of the light source when the integration value exceeds the reference value as a result of the comparison by the comparison unit.

20 Claims, 8 Drawing Sheets

| ISO SENSITIVITY | AMOUNT OF LIGHT (LEVEL) | INTEGRATION CIRCUIT OUTPUT VOLTAGE (V) | | |
|---|---|---|---|---|
| | | C pF | C/4 pF | C/16 pF |
| MAXIMUM | 0 | 5 | | |
| ISO100 STANDARD | -1 | 2.5 | | |
| ISO200 STANDARD | -2 | 1.25 | 5 | |
| ISO400 STANDARD | -3 | | 2.5 | |
| ISO800 STANDARD | -4 | | 1.25 | 5 |
| ISO1600 STANDARD | -5 | | | 2.5 |
| MINIMUM | -6 | | | 1.25 |

FIG.5

| AMOUNT OF LIGHT (LEVEL) | INTEGRATION CIRCUIT OUTPUT VOLTAGE (V) | | | REFERENCE D/A VALUE |
|---|---|---|---|---|
| | C pF | C/4 pF | C/16 pF | |
| 0.0 | 5.0 | | | 255 |
| -0.2 | 4.4 | | | 222 |
| -0.4 | 3.8 | | | 193 |
| -0.6 | 3.3 | | | 168 |
| -0.8 | 2.9 | | | 146 |
| -1.0 | 2.5 | | | 128 |
| -1.2 | 2.2 | | | 111 |
| -1.4 | 1.9 | | | 97 |
| -1.6 | 1.6 | | | 84 |
| -1.8 | 1.4 | | | 73 |
| -2.0 | | 5.0 | | 255 |
| -2.2 | | 4.4 | | 222 |
| -2.4 | | 3.8 | | 193 |
| -2.6 | | 3.3 | | 168 |
| -2.8 | | 2.9 | | 146 |
| -3.0 | | 2.5 | | 128 |
| -3.2 | | 2.2 | | 111 |
| -3.4 | | 1.9 | | 97 |
| -3.6 | | 1.6 | | 84 |
| -3.8 | | 1.4 | | 73 |
| -4.0 | | | 5.0 | 255 |
| -4.2 | | | 4.4 | 222 |
| -4.4 | | | 3.8 | 193 |
| -4.6 | | | 3.3 | 168 |
| -4.8 | | | 2.9 | 146 |
| -5.0 | | | 2.5 | 128 |
| -5.2 | | | 2.2 | 111 |
| -5.4 | | | 1.9 | 97 |
| -5.6 | | | 1.6 | 84 |
| -5.8 | | | 1.4 | 73 |
| -6.0 | | | 1.3 | 64 |

FIG.6

OPHTHALMOLOGIC APPARATUS

BACKGROUND OF THE INVENTION

1. Field of the Invention

The present invention relates to an ophthalmologic apparatus.

2. Description of the Related Art

In a conventional ophthalmologic apparatus such as a fundus camera, a light source such as a xenon tube is used as a light source for imaging a fundus of a target eye to be examined. Since the light source generally degrades with time, the imaging light amount varies even when the light emission of the light source is always stopped at the same timing.

Therefore, in order to control the imaging light amount, the light reflected from the target eye is monitored by a light receiving element such as a photo diode, and the output from the light receiving element is integrated by an integration circuit equipped with an operational amplifier and a capacitor. Then, there is a known technique of controlling the imaging light amount in a manner such that the light emission is stopped when the output voltage of the integration circuit becomes larger than a reference voltage based on the comparison between the output of the integration circuit and the reference voltage. Further, there is a known technique of changing the imaging light amount according to the sensitivity of a film used for an imaging operation, or the interest and preference of an examiner as to a portion to be imaged, by changing the reference voltage (see Japanese Patent Application Laid-Open No. 60-190930).

However, as an adjustment range of the imaging light amount becomes wider, a difference in light amount between the maximum light amount and the minimum light amount in the adjustment range of the imaging light amount increases. In addition, since the output voltage of the integration circuit decreases at it approaches the minimum light amount, the reference voltage which is compared with the output voltage of the integration circuit also decreases.

Further, a change in the output voltage of the integration circuit and the reference voltage in the vicinity of the minimum light amount is smaller, when the imaging light amount changes (for example, when the imaging light amount becomes a half), compared to a change in the output voltage of the integration circuit and the reference voltage in the vicinity of the maximum light amount when the imaging light amount changes (for example, when the imaging light amount becomes a half). More specifically, the resolutions of the output voltage of the integration circuit and the reference voltage are degraded as it approaches the minimum light amount. Further, when the voltage is low, the output voltage may be easily affected by noise.

Thus, the output voltage of the integration circuit and the value of the reference voltage become different from the desired values, so that the precision in the light amount control is degraded.

SUMMARY OF THE INVENTION

The invention is directed to adjusting a light emission amount with high precision.

According to an aspect of the present invention, an ophthalmologic apparatus includes an integration unit which integrates a light emission amount of a light source illuminating an target eye, an integral capacitance changing unit which changes a value of an integral capacitance of the integration unit according to the light emission amount necessary for imaging the target eye, a comparison unit which compares a reference value with an integration value integrated by the integration unit using the value of the integral capacitance changed by the integral capacitance changing unit, and a light emission control unit which stops the light emission of the light source when the integration value exceeds the reference value as a result of the comparison by the comparison unit.

The invention is not limited to the above-described feature, and the invention is also directed to the operation and the effect which are obtained by configurations illustrated in the exemplary embodiments to be described later and are not obtained by the conventional art.

According to the invention, the light emission amount may be adjusted with high precision.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Hereinafter, an ophthalmologic apparatus according to an exemplary embodiment of the invention will be described by referring to FIGS. 1 to 8.

Figure 1:
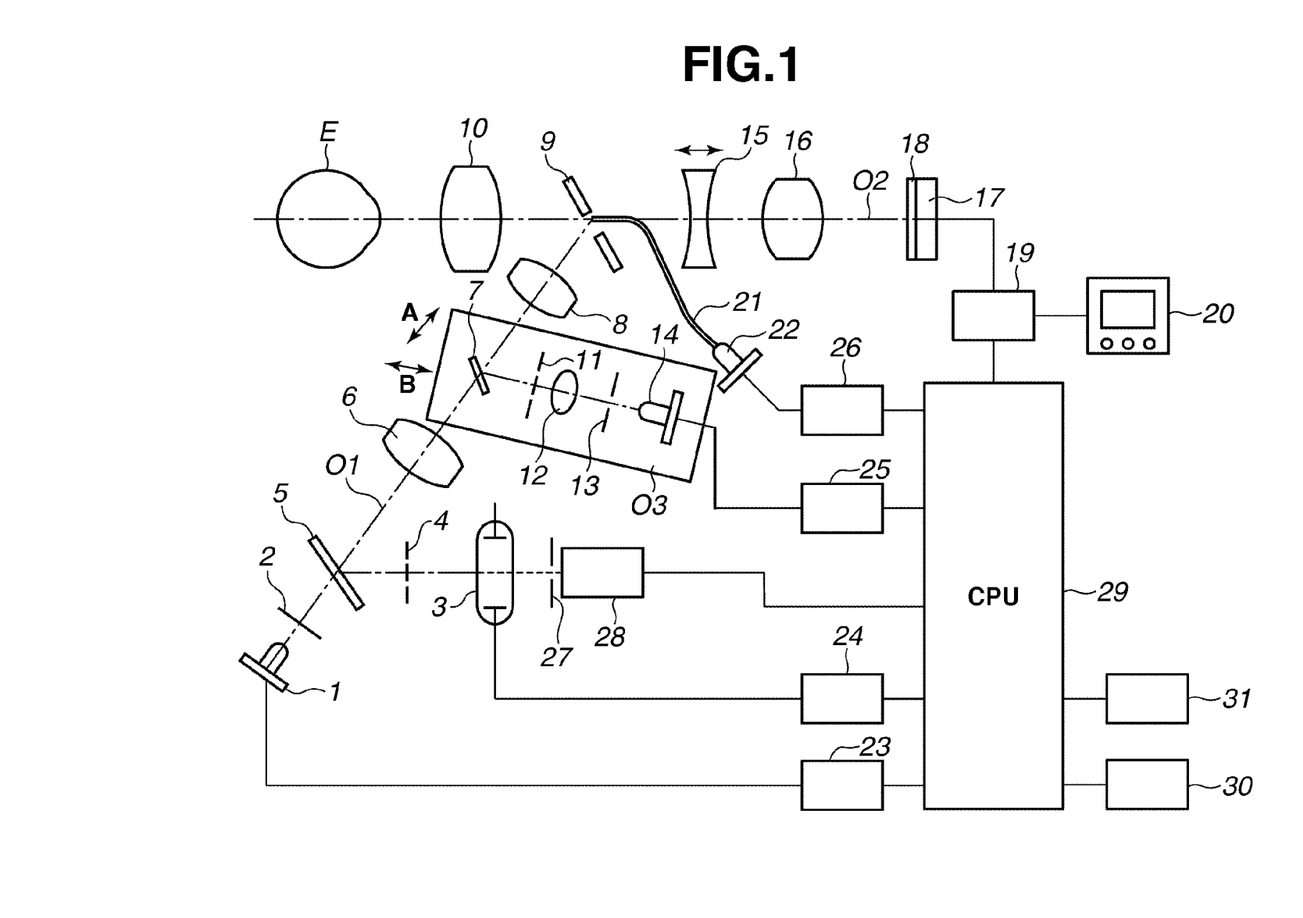
FIG. 1 is a diagram illustrating an example of a configuration of a fundus camera.

FIG. 1 illustrates an example of a configuration of a fundus camera of the exemplary embodiment. On the optical path from an infrared light emitting diode (LED) 1 of an infrared observation light source to an objective lens 10, a diaphragm 2 having an annular opening, a dichroic mirror 5 that transmits infrared light and reflects visible light, a relay lens 6, a mirror 7, a relay lens 8, and a perforated mirror 9, are in this order arranged.

On the optical path from a xenon tube 3 serving as an imaging light source that emits visible light to the objective lens 10, a diaphragm 4 having an annular opening, the dichroic mirror 5, the relay lens 6, the mirror 7, the relay lens 8, and the perforated mirror 9 are in this order arranged. The relay lens 6, the mirror 7, the relay lens 8, and the perforated mirror 9 constitute a fundus illumination optical system O1.

In the reflection direction of the mirror 7, a diaphragm 11, a lens 12, a focusing index 13, and an infrared LED 14 serving as a focusing index light source are arranged, which constitutes a focusing index projection optical system O3.

The focusing index projection optical system O3 moves in the direction of the optical axis (the direction of A of the drawing) in conjunction with a focusing lens 15. In a still image capturing mode, the focusing index projection optical system moves in a direction (the direction of B of the drawing) deviating from the optical axis driven by a driving system (not illustrated) and retracts from the illumination optical system O1.

On the optical path in the transmission direction of the perforated mirror 9, the focusing lens 15, an imaging lens 16, and an imaging unit 17 are arranged, which constitutes a fundus imaging optical system O2. The output of the imaging unit 17 is sequentially connected to an image signal processing unit 19 and a display unit 20. An infrared LED 22 as an aligning index light source is connected to the perforated mirror 9 through an optical fiber 21.

Filters 18 arranged in a mosaic shape of three colors of R (red), G (green), and B (blue) are arranged on each pixel of the imaging unit 17, and the R filter can transmit infrared light. Each pixel has sensitivity for the light of any one of R, G, and B, and the R pixel has sensitivity for infrared light.

When performing an infrared observation, the image signal processing unit 19 generates monochrome moving image data by using the output of the R pixel and outputs a moving image to the display unit 20. In a color still image capturing mode, the image signal processing unit 19 generates a color still image by using the outputs of the respective pixels of R, G, and B. The generated image is recorded in a recording unit 31 through a central processing unit (CPU) 29. The imaging unit 17 may change the ISO sensitivity by the instruction from the CPU 29.

The infrared LED 1 is connected to an LED driving circuit 23, the imaging xenon tube 3 is connected to a xenon tube driving circuit 24, the infrared emission LED 14 is connected to an LED driving circuit 25, and the infrared LED 22 is connected to an LED driving circuit 26. The LED driving circuit 23, the xenon tube driving circuit 24, the LED driving circuit 25, the LED driving circuit 26, the light amount detection unit 28, the imaging unit 17, the image signal processing unit 19, the operation unit 30, and the recording unit 31 are respectively connected to the CPU 29.

The LED driving circuit 23 controls the driving of the infrared LED 1 based on the instruction of the CPU 29. The xenon tube driving circuit 24 controls the driving of the xenon tube 3 based on the instruction of the CPU 29. The LED driving circuit 25 controls the driving of the infrared emission LED 14 based on the instruction of the CPU 29. The LED driving circuit 26 controls the driving of the infrared LED 22 based on the instruction of the CPU 29.

The light amount detection unit 28 is disposed in the rear of the xenon tube 3, and is configured to receive a part of the light flux exiting from the xenon tube 3 through the diaphragm 27. Specifically, the light amount detection unit 28 is disposed on the optical axis opposite to the optical axis direction in which the light exiting from the xenon tube 3 is directed toward the target eye E to be examined. The light amount detection unit 28 detects the amount of light exiting from the xenon tube 3. The diaphragm 27 includes a transmission portion which is provided on the optical axis of the xenon tube 3 so that light is transmitted therethrough. The portion other than the transmission portion of the diaphragm is configured, for example, such that light exiting from the xenon tube 3 to the opposite side of the target eye is reflected toward the target eye. For example, aluminum or the like is deposited on the diaphragm 27 so as to reflect light.

Figure 2:
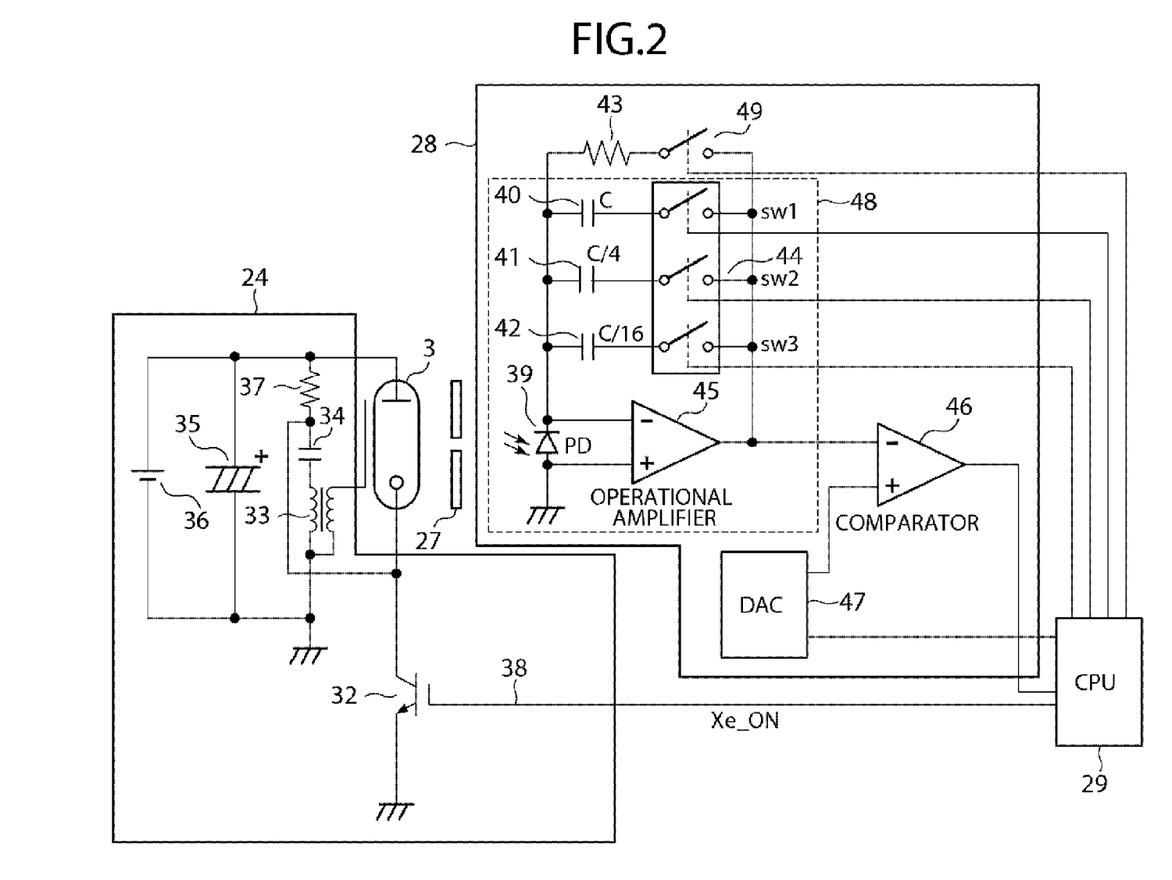
FIG. 2 is a diagram illustrating an example of an electric circuit of a xenon tube driving circuit and a light amount detection unit.

FIG. 2 is a diagram illustrating an example of a configuration of an electric circuit of the xenon tube driving circuit 24 and the light amount detection unit 28. The xenon tube driving circuit 24 includes an insulated gate bipolar transistor (IGBT) 32, a trigger transformer 33, a trigger capacitor 34, a main capacitor 35, a power supply 36, and a resistor 37. The main capacitor 35 is charged to a high voltage (for example, 300 V) by the power supply 36. The trigger capacitor 34 is also charged by the power supply 36 through the resistor 37.

When the output of the Xe_ON signal output from the CPU 29 becomes a high level (Hi), the IGBT 32 is turned on, that is, the IGBT 32 becomes a connected state, so that the charges of the trigger capacitor 34 are discharged. Due to the discharge of the electric charges, a current flows to a coil on the left side of the trigger transformer 33. When the current flows to the coil on the left side of the trigger transformer 33, a high voltage is generated in a coil on the right side of the trigger transformer 33, so that a trigger signal is applied to the xenon tube 3, and a current flows from the main capacitor 35 to the xenon tube 3. When the current flows to the xenon tube 3, the light emission of the xenon tube 3 is started. When the Xe_ON signal becomes a low level (Low) after the light emission starts, the IGBT 32 is turned off, so that the current of the xenon tube 3 is interrupted and the light emission is stopped.

The light amount detection unit 28 includes a reset resistor 43, a comparator 46, a D/A converter 47, an integration circuit 48, and an analog switch 49. The integration circuit 48 includes a photo diode 39, integration capacitors 40 to 42, an operational amplifier 45, and an analog switch 44. The analog switch 44 includes a SW1, a SW2, and a SW3.

The integration circuit 48 outputs a voltage according to (for example, in proportion to) the light amount of the xenon tube 3 in a manner such that at least one of the integration capacitors 40 to 42 is charged by the photoelectric current generated according to (for example, in proportion to) the light amount of the xenon tube 3 which flows through the photo diode 39. Specifically, the integration circuit 41 integrates the current of the photo diode 39. In other words, the integration circuit 41 integrates the light emission amount of the xenon tube 3. That is, the integration circuit 48 is an example of an integration unit which integrates the light emission amount of the light source illuminating the target eye.

For example, when the capacitance of the integration capacitor 40 is denoted by C, the capacitance of the integration capacitor 41 becomes ¼ of C, and the capacitance of the integration capacitor 42 becomes ¹⁄₁₆ of C. In other words, the integration unit is equipped with plural selectable integral capacitors having different values.

However, the integration capacitors 40 to 42 are not limited to those having these values, and the other values may be used. The number of the integration capacitors may be four or more, or may be two. A method of determining the values of the integration capacitors 40 to 42 will be described later.

The value of the integration capacitor which is used in the integration circuit 48 is changed by controlling the analog switch 44. More specifically, the sensitivity of the integration circuit 48 for the light emission amount of the xenon tube 3 is changed by changing the value of the integration capacitor. When the analog switch 49 is turned on, the charges of the integration capacitors 40 to 42 may be reset through the reset resistor 43. That is, when the analog switch 49 is turned on, the output of the integration circuit 48 may be reset. The reset resistor 43 may not be provided in the circuit. The analog switch is, for example, a MOS switch.

The photo diode 39 is provided on the optical axis of the xenon tube 3 in the direction opposite to the direction directed from the xenon tube 3 toward the target eye E. More specifically, the photo diode 39 is an example of a photo diode which is provided on the optical axis of the light source in the direction opposite to the direction directed from the light source toward the target eye. The xenon tube 3 is optimized so as to illuminate the target eye E, and the amount of light other than that on the optical axis of the light source is unstable. For this reason, since the light amount may be detected on the optical axis of the xenon tube 3 by disposing the photo diode 39 as described above, the light amount may be stably detected.

The D/A converter 47 outputs a reference voltage (reference value) which is compared with the output of the integration circuit 48 when stopping the light emission of the xenon tube 3 based on the control of the CPU 29. Specifically, the D/A converter 47 outputs the voltage according to the input D/A value as the reference voltage. Since the reference voltage which stops the light emission of the xenon tube 3 is output, the D/A value which is input to the D/A converter 47 may be referred to as a stop D/A value.

The output of the D/A converter 47 is connected together with the output of the operational amplifier 45, to the input of the comparator 46 The comparator 46 performs the comparison between the output voltage of the integration circuit 48 and the output voltage of the D/A converter 47. More specifically, the comparator 46 is an example of a comparison unit which compares the reference value with the integration value integrated by the integration unit using the value of the integration capacitance changed by the integral capacitance changing unit.

The output voltage of the integration circuit 41 and the output voltage of the D/A converter 47 are input to the comparator 46. When the output voltage of the integration circuit 48 is smaller than the output voltage of the D/A converter 47, Hi is output from the comparator 46. When the output voltage of the integration circuit 48 is larger than the output voltage of the D/A converter 47, for example, Low is output from the comparator 46. The voltage which is output from the comparator 46 may be Low when the output voltage of the integration circuit 48 is smaller than the output voltage of the D/A converter 47, and may be Hi when the output voltage of the integration circuit 48 is larger than the output voltage of the D/A converter 47.

The analog switches 44 and 49 and the D/A converter 47 are connected to the CPU 29, and the output of the comparator 46 is connected to the CPU 29.

Next, an example of a method of determining the values of the integration capacitors 40 to 42 of the integration circuit 48 will be described by referring to FIGS. 3 to 5.

Figure 3:
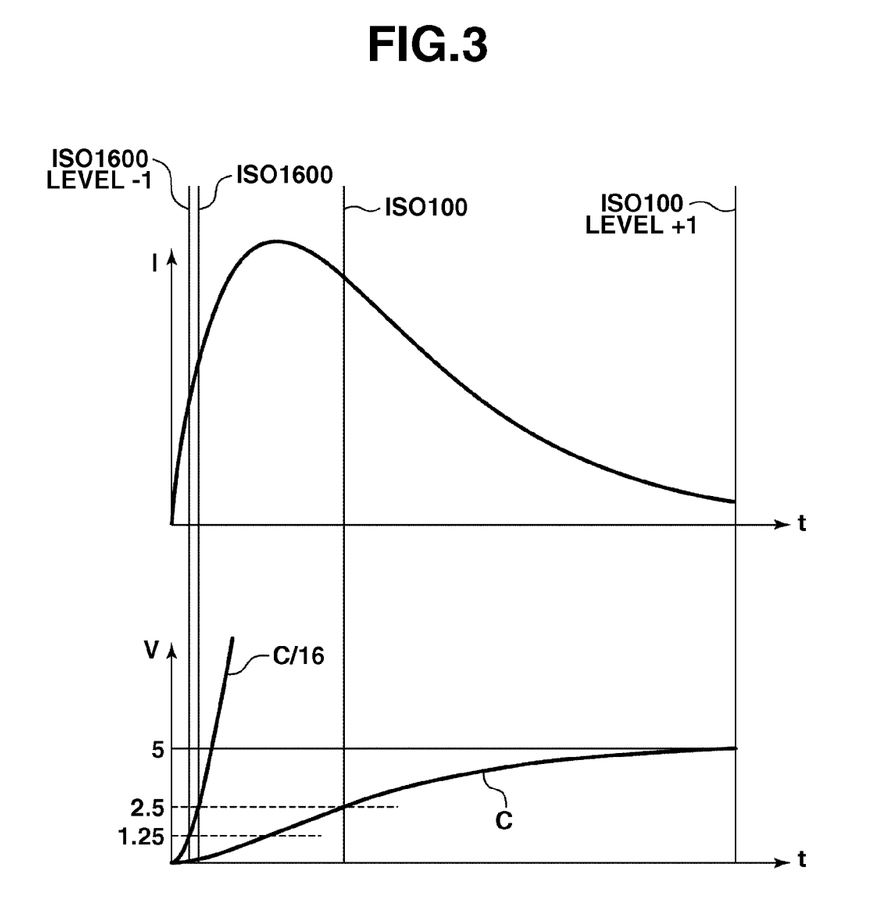
FIG. 3 is a diagram illustrating an example of a relation between a light emission amount and an output voltage of an integration circuit.

FIG. 3 is a diagram illustrating an example of a relation between the light emission amount of the xenon tube 3 and the output voltage of the integration circuit 48. In FIG. 3, the upper side indicates the photoelectric current which is generated according to (for example, in proportion to) the light amount of the xenon tube 3 and flows through the photo diode 39. In FIG. 3, the lower side indicates the output voltage of the integration circuit 48 which is obtained when integrating the photoelectric current flowing through the photo diode 39 by the integration circuit 48.

For example, in a case where the ISO sensitivity of the imaging unit 17 may be set from 100 to 1600, the light amount correction range is Level ±1 of the standard light amount of each ISO sensitivity. In addition, when the value of the ISO sensitivity becomes twice as much, the necessary light amount becomes ½. For example, when the light amount increases by Level 1, the light amount becomes twice as much. When the light amount decreases by Level 1, the light amount becomes ½. In this case, the maximum light amount is obtained by correction of Level +1 of the standard light amount of ISO100. For example, the capacitance of the integration capacitor is determined so that the output voltage of the integration circuit 48 becomes 5 V at the maximum light amount, and the capacitance is denoted by CpF.

If the current of the xenon tube 3 is interrupted when the output of the integration circuit 48 becomes 5 V, the maximum light emission amount necessary for the imaging operation may be obtained. Since the light amount necessary for the imaging operation is ½ of the maximum light amount at the standard light amount of ISO100, it is possible to obtain the necessary light emission amount which interrupts the current of the xenon tube 3 when the integration circuit output voltage exceeds 2.5 V.

The standard light amount of ISO1600 becomes ¹⁄₁₆ of the standard light amount of ISO100, and the output voltage of the integration circuit 48 for obtaining the standard light amount of ISO1600 becomes 156 mV. In the correction of Level −1 of the standard light amount of ISO1600 as the minimum light amount, the output voltage of the integration circuit 48 becomes ½ of the standard light amount of ISO1600. Thus, the output voltage of the integration circuit 48 for obtaining the minimum light amount becomes 78 mV, and this is a very small value compared to 5 V. Since the current of the xenon tube 3 does not need to be interrupted when the output voltage of the integration circuit 48 exceeds 78 mV, the output voltage of the D/A converter 47 also becomes 78 mV. Thus, the outputs of the integration circuit 48 and the D/A converter 47 are easily affected by noise or the like. For example, when the output of the integration circuit 48 becomes 80 mV due to the noise when the output of the integration circuit 48 is 50 mV, the light emission of the xenon tube 3 is stopped at that time point, so that the light amount may not be precisely adjusted.

As illustrated in the lower stage of FIG. 3, when the capacitance of the integration capacitor is set to C/16 pF, the output voltage of the integration circuit 48 becomes 16 times the output voltage generated when using the integration capacitor of the capacitance CpF. Thus, the output voltage of the integration circuit 48 becomes 2.5 V at the standard light amount of ISO1600, and becomes 1.25 V even in the case of the correction of Level −1 of ISO1600. Thus, compared to the case where the value of the integration capacitor is not changed, the outputs of the integration circuit 48 and the D/A converter 47 are hardly affected by noise or the like. In the present embodiment of the invention, the change of the output voltage of the integration circuit according to the value of the integration capacitor is utilized.

Figure 4:
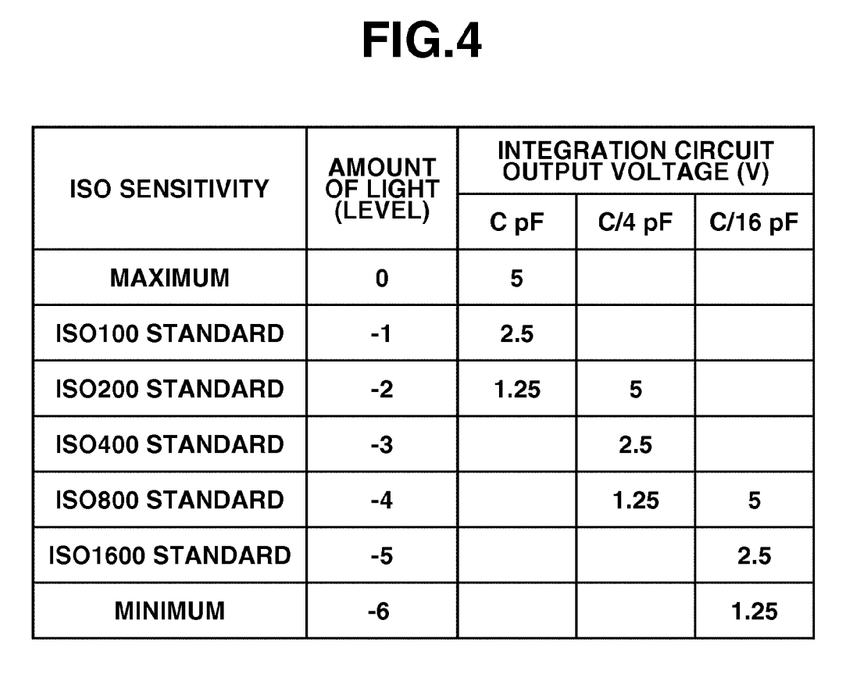
FIG. 4 is a diagram illustrating an example of a relation between ISO sensitivity and an output voltage of an integration circuit caused by a capacitance of an integration capacitor.

FIG. 4 is a diagram illustrating an example of a relation between the light emission amount and the output voltage of the integration circuit owing to the capacitance of the integration capacitor. As an example, it is assumed that the range of the output of the D/A converter 47 is from 0 to 5V. In FIG. 4, when the maximum light amount (at the time when the light amount is corrected by Level 1 at ISO100) is set to Level 0, the minimum light amount (at the time when the light amount is corrected by Level −1 at ISO1600) becomes Level −6, so that the light amount adjustment range is divided into six levels. In FIG. 4, the unit of the light amount is described as the "level". The "level" indicates that the light amount becomes twice the reference light amount when the light amount increases by Level 1 based on the light amount at Level 0. In this case, the maximum light amount in the color imaging mode is set to Level 0, but the invention is not limited thereto. The light amount in other cases may be set to Level 0.

For example, when there are three types of integration capacitors having different capacitances, 6 levels/3=2. The light amount adjustment range for the integration circuit 48 using one integration capacitor becomes two levels. That is, when the light amount adjustment range is divided by a number of types of integration capacitors having different capacitances, the light amount adjustment range which is determined by the integration circuit 48 using one integration capacitor is determined. With this configuration, the light amount adjustment range for the integration circuit 48 using one integration capacitor becomes even. Thus, it is possible to prevent the output voltage of the integration circuit 48 using a specific integration capacitor from becoming lower than the output voltage of the integration circuit 48 using the other integration capacitors, and reduce an influence of the noise or the like on the output of the integration circuit 48.

Next, the capacitance ratio of each integration capacitor is determined. In the above-described example, a difference in light amount between two levels becomes 2^2=4, so that the capacitance ratio of each integration capacitor becomes 4, where X^Y indicates X to the power of Y. More specifically, a difference of light amount in the light amount adjustment range for the integration circuit 48 using one integration capacitor is set to the capacitance ratio of each integration capacitor.

As described above, the values of the plural integral capacitances are determined based on the light amount adjustment range (for example, six levels) as the range of the adjustment of the light emission amount of the light source, and the number of the plural integral capacitances (for example, three).

As described above, when the capacitance of each integration capacitor is determined, the output voltage of the integration circuit 48 is as illustrated in FIG. 4. As can be seen from FIG. 4, when the output voltage of the integration circuit becomes 1.25 V in a case where the capacitance of the integration capacitor is CpF, the output of the integration circuit becomes 5 V when the capacitance of the integration capacitor is C/4 pF. In this way, when the specific integration capacitor is used and the output of the integration circuit 48 is degraded, the output of the integration circuit 48 using the other capacitors becomes 5 V which is the maximum value of the output voltage of the D/A converter 47.

As understood from FIG. 4, the value of the integral capacitance is changed to be a small value as the light emission amount necessary for imaging the target eye decreases. More specifically, even when the light emission amount necessary for the imaging operation decreases, the value of the integration capacitor decreases so that the output of the integration circuit 48 does not decrease.

Figure 5:
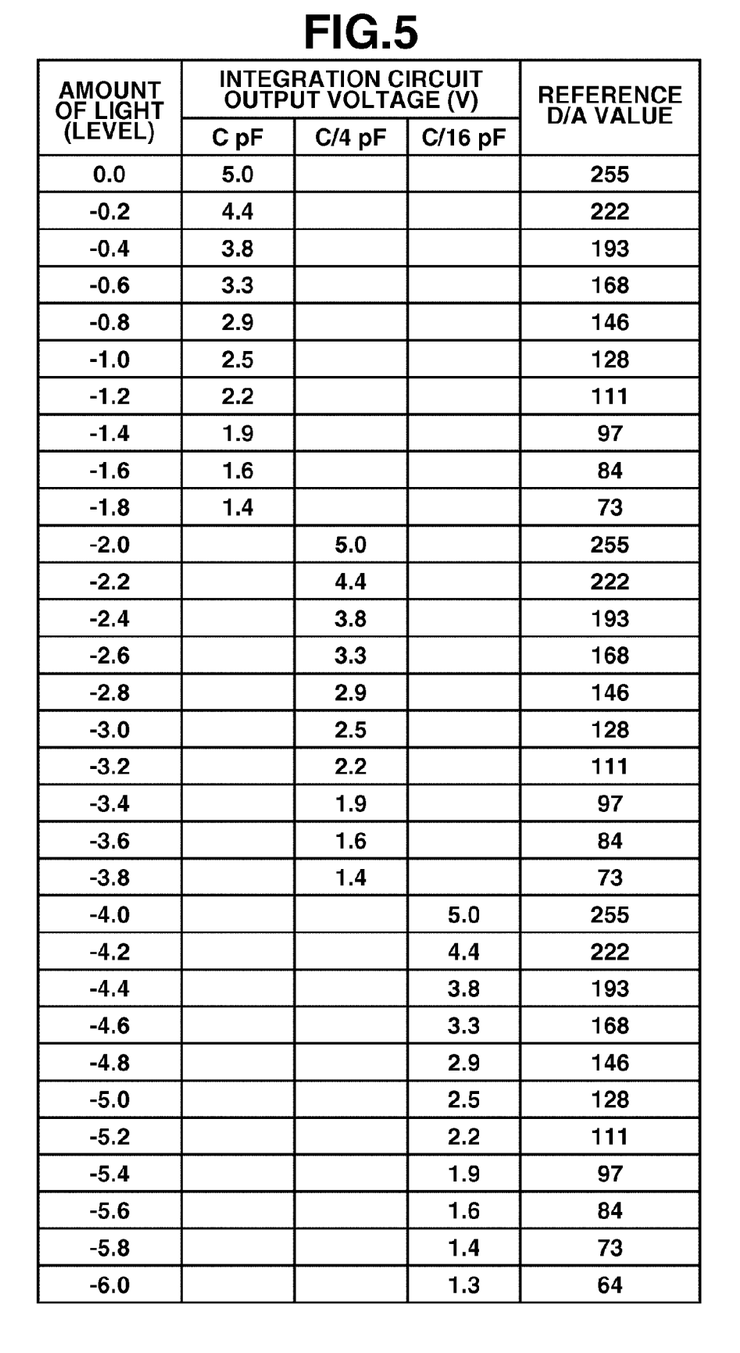
FIG. 5 is a diagram illustrating an example of a table in which a light emission amount, a capacitance of an integration capacitor, and a D/A value are correlated with each other.

FIG. 5 is an example of a table illustrating a relation among the light amount obtained when the light amount adjustment step for the table of FIG. 4 is Level 0.2, the capacitance of the integration capacitor, and the D/A value of the D/A converter 47 outputting the reference voltage.

When the light amount decreases by Level 0.2, the output voltage of the integration circuit decreases at the rate of 2^(−0.2). In a case where the range of the output of the D/A converter 47 is 0 to 5 V and the input is 8 bit, the relation between the D/A value and the output voltage becomes V=5× D/A value/255. Accordingly, the relation between the integration circuit output voltage and the D/A value becomes the one as shown in the table of FIG. 5. More specifically, since the output of the integration circuit 48 changes according to a change in the integration capacitor, the reference D/A value changes according to a change in the integration capacitor. Since the reference D/A value changes, the output voltage of the D/A converter 46 also changes. In other words, the reference value is determined according to the value of the integral capacitance changed by the integral capacitance changing unit.

As described above, the capacitance ratio (the capacitance value) of the integration capacitor is determined, and the table illustrated in FIG. 5 is created. The created table is recorded in a recording device such as a memory which may be referred to by the CPU 29.

The capacitance ratio of the integration capacitor and the table illustrated in FIG. 5 are determined by, for example, the designer of the apparatus.

Figure 6:
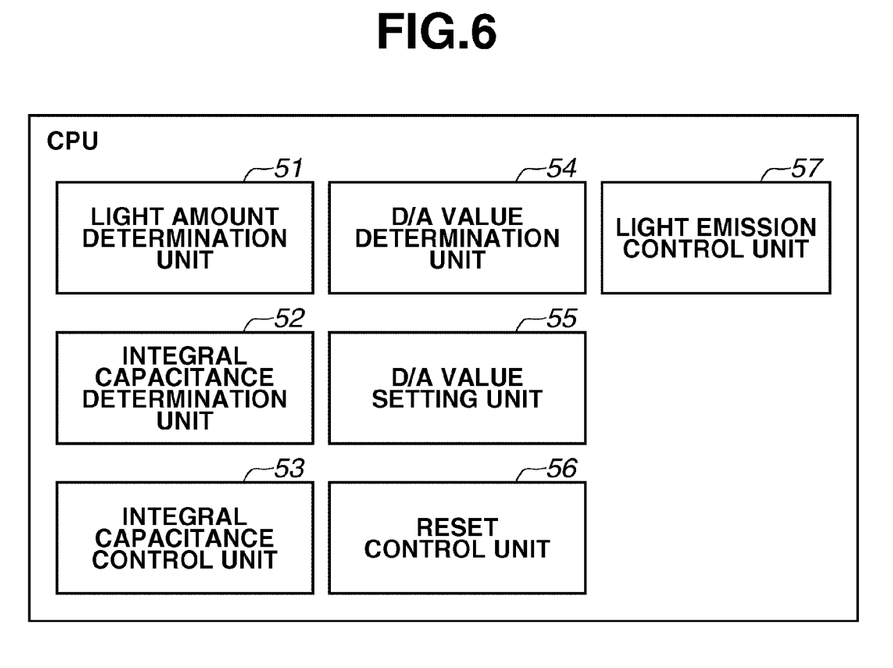
FIG. 6 is a diagram schematically illustrating an example of a function of a CPU.

FIG. 6 is a diagram schematically illustrating a function of the CPU 29. The CPU 29 serves as a light amount determination unit 51, an integral capacitance determination unit 52, an integral capacitance control unit 53, a D/A value determination unit 54, a D/A value setting unit 55, a reset control unit 56, and a light emission control unit 57 by executing a program recorded in a memory (not illustrated) or the like.

The light amount determination unit 51 determines the light emission amount of the xenon tube 3 based on the ISO sensitivity input through the operation unit 30. In other words, the light amount determination unit 51 determines the amount of light radiated from the xenon tube 3 to the target eye E, based on the ISO sensitivity. The light amount determination unit 51 determines the amount of light radiated from the xenon tube 3 to the target eye E based on the ISO sensitivity and the light amount adjustment value. Specifically, the light amount determination unit 51 determines the light amount based on the table in which the ISO sensitivity and the necessary light amount are correlated with each other.

For example, when the ISO sensitivity of 100 and the adjustment of the light amount of Level −0.2 are input through the operation unit 30, the light amount determination unit 51 determines the light amount as Level −1.2.

The integral capacitance determination unit 52 determines the value of the integration capacitor of the integration circuit 48 based on, for example, the light amount which is determined by the light amount determination unit 51. Specifically, the integral capacitance determination unit 52 determines the value of the integration capacitor by using the table illustrated in FIG. 5.

For example, when the light amount is determined as Level −1.2 by the light amount determination unit 51, the integral capacitance determination unit 52 determines the value of the integration capacitor as CpF. For example, when the light amount is determined as Level −3.0 by the light amount determination unit 51, the integral capacitance determination unit 52 determines the capacitance of the integration capacitor as C/16 pF.

The operation of the integral capacitance determination unit 52 is not limited thereto. For example, the value of the integration capacitor may be directly determined based on the ISO sensitivity input through the operation unit 30 or the ISO sensitivity and the light amount adjustment value without using the light amount determined by the light amount determination unit 51.

The integral capacitance control unit 53 controls the switching of the analog switch 44 based on the value of the integration capacitor determined by the integral capacitance determination unit 52. For example, when the value of the integration capacitor is determined as CpF by the integral capacitance determination unit 52, the integral capacitance control unit 53 turns on the SW1 connected to the integration capacitor 40, and turns off the SW2 and the SW3. By this control, the value of the integration capacitor of the integration circuit 48 becomes CpF.

More specifically, the integral capacitance control unit 53 is an example of an integral capacitance changing unit which changes the value of the integral capacitance of the integration unit according to the light emission amount necessary for imaging the target eye. The integral capacitance control unit 53 changes the value of the integral capacitance by selecting one integral capacitance from a plurality of integral capacitances. As understood from FIG. 4, the integral capacitance control unit 53 which is an example of the integral capacitance changing unit, changes the value of the integral capacitance to a small value as the light emission amount necessary for imaging the target eye decreases.

The integral capacitance control unit 53 outputs a Hi signal to the SW1 so that the SW1 is turned on, and outputs a Low signal to the SW2 and the SW3 so that the SW2 and the SW3 are turned off. However, as the analog switches 44 and 49, a switch may also be used which is turned off when receiving a Hi signal and is turned on when receiving a Low signal.

The D/A value determination unit 54 determines the reference D/A value as the value of the signal input to the D/A converter 47 based on the light amount determined by the light amount determination unit 51. Specifically, the D/A value determination unit 54 determines the reference D/A value by referring to the table illustrated in FIG. 5. For example, when the light amount is determined as Level −1.2 by the light amount determination unit 51, the D/A value determination unit 54 determines the reference D/A value as 111. The operation of the D/A value determination unit 54 is not limited thereto. For example, the reference D/A value may be directly determined based on the ISO sensitivity input through the operation unit 30 and the ISO sensitivity and the light amount adjustment value without using the light amount determined by the light amount determination unit 51.

The D/A value setting unit 55 sets the D/A value to the D/A converter 47. Specifically, the reference D/A value which is determined by the D/A value determination unit 54 is set (input) to the D/A converter 47.

The reset control unit 56 resets the output of the integration circuit 48. Specifically, the reset control unit 56 resets the output of the integration circuit 48 in a manner such that the analog switch 49 is turned on so as to discharge the electric charges of the integration capacitors 40 to 42 when the output of the comparator 46 is reversed due to the output of the integration circuit 48 exceeding the output of the D/A converter 47. The reset control unit 56 turns off the analog switch 49 when the output of the comparator 46 is reversed due to the output of the integration circuit 48 lower than the output of the D/A converter 47, by resetting of the output of the integration circuit 48. The reset control unit 56 outputs a Hi signal to the analog switch 49 so as to turn on the analog switch 49, and outputs a Low signal to the analog switch 49 so as to turn off the analog switch 49. However, as the analog switch 49, a switch may also be used which is turned off when receiving a Hi signal and is turned on when receiving a Low signal.

The light emission control unit 57 controls the light emission of the xenon tube 3. When the imaging operation is started by the operator through the operation unit 30, the light emission control unit 57 starts the light emission of the xenon tube 3 by setting the Xe_ON signal to be Hi so that the IGBT 32 is turned on. The output of the comparator 46 shows a Hi level at the time point at which the imaging operation is started.

The light emission control unit 57 stops the light emission of the xenon tube 3 when it detects that the output of the comparator 57 becomes Low, by setting the Xe_ON signal to be Low. More specifically, the light emission control unit 57 is an example of a light emission control unit which stops the light emission of the light source when the integration value exceeds the reference value as a result of comparison by the comparison unit.

Figure 7:
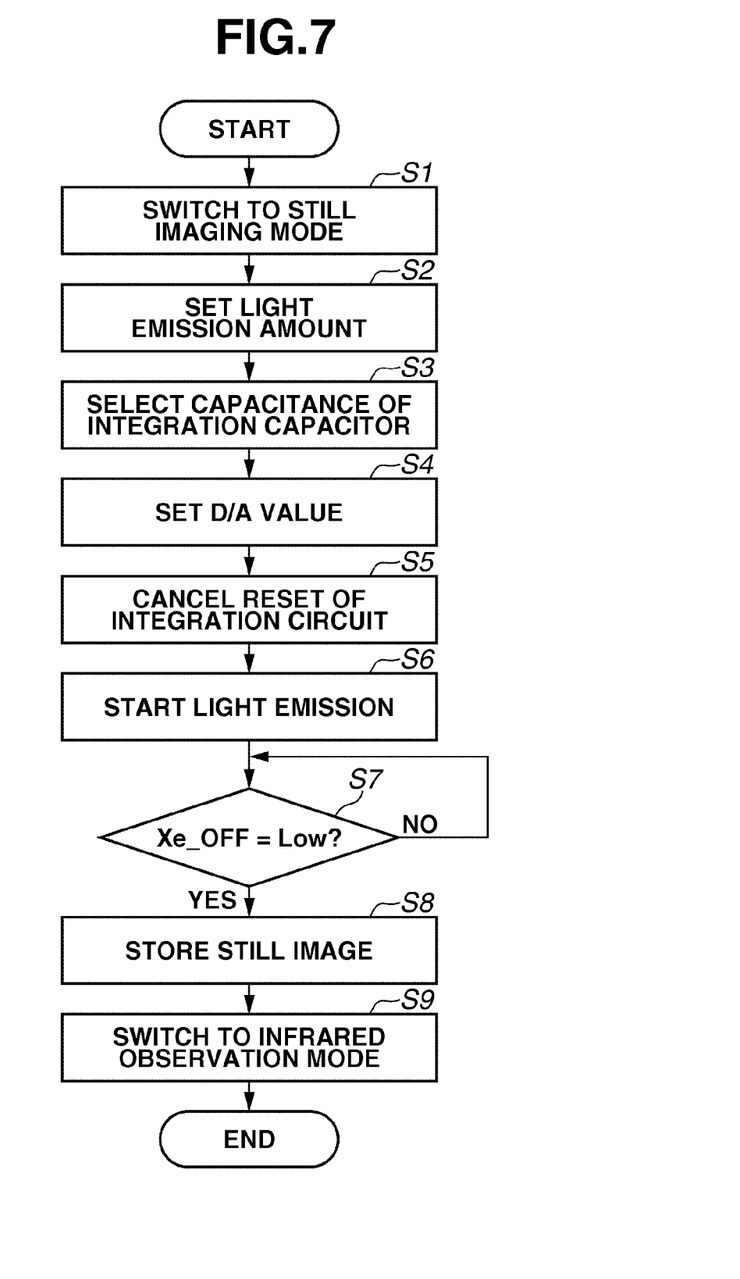
FIG. 7 is a flowchart illustrating an example of an operation from the start of an imaging operation to the stop of a light emission of a xenon tube.

The operation of the ophthalmologic apparatus with the above-described configuration will be described by referring to the flowchart illustrated in FIG. 7.

First, the operation up to the imaging operation will be described. In the initial state (the infrared fundus observation mode), for example, the CPU 29 outputs Low as the Xe_ON signal, the analog switches 44 and 49 are turned on, and the integration circuit 48 is in a reset state. The output of the operational amplifier 45 is 0 V, the output of the D/A converter 47 is set to a voltage larger than 0, and the output signal of the comparator 46 is Hi.

In the initial state, the operator sets the ISO sensitivity and the light amount adjustment value during the imaging operation by operating a sensitivity setting SW and a light amount adjustment switch (not illustrated) of the operation unit 30. When the ISO sensitivity is set, the CPU 29 changes the ISO sensitivity of the imaging unit 17. Next, the alignment between the fundus camera and the target eye E is performed by the fundus image of the target eye E and the positioning index image. The fundus image of the target eye E is illuminated by the infrared LED 1 of the infrared observation light source and is displayed on the display unit 20. The positioning index image is projected to the cornea of the target eye E by the infrared LED 22 of the aligning index light source.

The focus operation is performed by the index image of the infrared LED 14 of the focusing index light source. When the alignment and the focus operation are completed, the operator starts the imaging operation by pressing an imaging switch (not illustrated) of the operation unit 30.

Next, the operation from the start of the imaging operation to the stop of the light emission of the xenon tube 3 will be described.

In step 1, in order to switch the infrared observation mode to the still image capturing mode, the CPU 29 turns off the infrared LED 1, the infrared LED 22, and the infrared LED 14 and retracts the focusing index projection optical system O2 from the optical axis of the illumination optical system O1.

In step 2, the light amount determination unit 51 determines the light emission amount from the set ISO sensitivity and the light amount adjustment value. If the ISO sensitivity is 100 and the light amount adjustment value is Level −0.2, the light amount determination unit 51 determines the light amount as Level −1.2 since the standard light amount of ISO100 of FIG. 4 becomes Level −1 and the light amount adjustment value becomes Level −0.2.

In step 3, the integral capacitance determination unit 52 determines the capacitance of the integration capacitor from the table of FIG. 5 based on the level number of the determined light amount. Since the current light emission amount is Level −1.2, the integral capacitance determination unit 52 selects the integration capacitor of the capacitance CpF. Since the capacitor of the capacitance CpF is the integration capacitor 40 of FIG. 2, the integral capacitance control unit 53 turns off the SW2 and the SW3 of the analog switch 44 so that the integration capacitors 41 and 42 are disconnected from the integration circuit.

In step 4, the reference D/A value determination unit 54 determines the reference D/A value as 111 from the table of FIG. 5 when the light emission amount is Level −1.2, and the reference D/A value setting unit 55 sets the reference D/A value to the D/A converter 47.

In step 5, the reset control unit 56 turns off the analog switch 49 so as to cancel the resetting of the integration circuit 48.

In step 6, the light emission control unit 57 sets the Xe_ON signal to Hi. Accordingly, when the IGBT 32 is turned on, a trigger signal is input to the xenon tube 3, so that the light emission is started. The integration circuit 48 integrates the light emission amount of the xenon tube 3.

In step 7, the CPU 29 waits until the output signal of the comparator 46 becomes Low due to the output voltage of the integration circuit 48 exceeding the reference voltage output from the D/A converter 46. Then, the light emission control unit 57 sets the Xe_ON signal to Low when the output of the comparator 46 becomes Low. Accordingly, the IGBT 32 is turned off, so that the light emission of the xenon tube 3 is stopped.

In step 8 after the light emission of the xenon tube 3 stops, the CPU 29 stores the still image, which is generated by the image signal processing unit 19 from the output of the imaging unit 17, in the recording unit 31.

In step 9, the current mode switches to the infrared observation mode.

The operation from the light emission of step 5 to the stop of the light emission of step 6 will be described by referring to the timing chart of FIG. 8.

Figure 8:
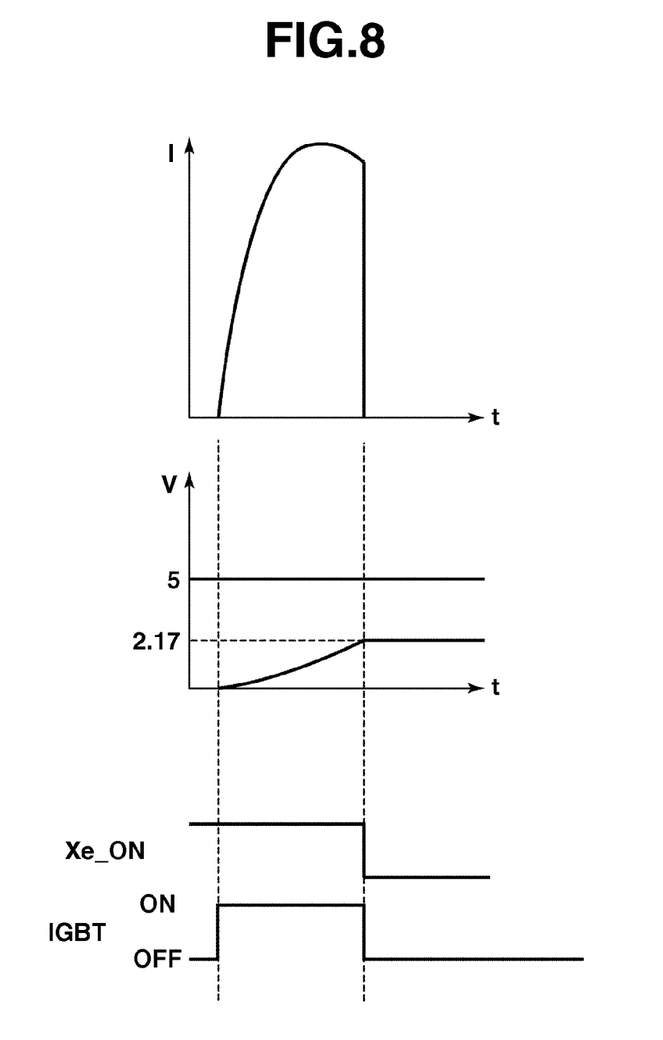
FIG. 8 is a timing chart illustrating an example from the start of the light emission to the stop of the light emission.

The graph of the upper stage of FIG. 8 illustrates the light amount, and the graph of the middle stage illustrates the output voltage of the integration circuit 48. When the light emission control unit 57 sets the Xe_ON signal to Hi, the IGBT 32 is turned on, so that the light emission is started. A voltage which is generated according to the integration value of the light emission with time is output from the integration circuit 48.

In the D/A converter 47, the D/A value is set as 111, and 2.17 V is output. When the output of the integration circuit 48 becomes equal to or more than 2.17 V, the output of the comparator 46 changes from Hi to Low. Then, the light emission control unit 57 sets the Xe_ON signal to be Low so that the IGBT 32 is turned off. As a result, the current of the xenon tube 3 is interrupted, and the light emission is stopped. Accordingly, the target light emission amount may be controlled.

In this way, according to the ophthalmologic apparatus of the present exemplary embodiment, since the output of the integration circuit and the reference voltage are not degraded compared to the case where the value of the integration capacitor is not changed, it is possible to reduce an influence caused by noise or the like on the output voltage of the integration circuit and on the reference voltage to be compared with the output voltage of the integration circuit. Thus, the light emission amount may be adjusted with high precision compared to the case where the value of the integration capacitor is not changed.

In this connection, there may be a method which uses a logarithmic amplifier in the integration circuit so as to deal with the broad light amount range without changing the value of the integration capacitor. However, the logarithmic amplifier increases the number of components, which increases the cost of the apparatus and complicates the apparatus.

There is also a method in which an optical light amount restriction members such as a filter are switched in front of the photo diode according to the light amount, but the switching mechanism is needed therefor, and the apparatus increases in cost and becomes complicated.

According to the ophthalmologic apparatus, the light emission amount may be adjusted with high precision in the broad range while preventing the apparatus from increasing in cost and becoming complicated as described above.

The disclosed technique is not limited to the above-described exemplary embodiment, and may be implemented in various modified forms without departing from the spirit of the exemplary embodiment.

For example, in the table illustrated in FIG. 5, the light amount is divided by the unit of Level 0.2, but the invention is not limited thereto. For example, the light amount may be divided by the narrower level or the wider level. For example, the light amount may be divided by Level 1/10 or Level 1.

In the tables illustrated in FIGS. 4 and 5, the unit of the light amount is indicated by the "level", but the invention is not limited thereto. For example, the other units of measure may be used.

In FIG. 4, the ISO value is 100 to 1600, but the invention is not limited thereto. For example, the other values may be used.

In the example illustrated in FIGS. 4 and 5, it is described that the light amount becomes twice when the light amount adjustment value increases by Level 1, but the invention is not limited thereto. When the light amount increases by Level 1, the light amount may become three times. Similarly, in the example illustrated in FIG. 4, it is described that the light amount becomes ½ times when the light amount adjustment value decreases by Level 1, but the invention is not limited thereto. For example, the light amount may become ⅓ times when the light amount decreases by Level 1.

In the exemplary embodiment, the observation light source is an LED, but the invention is not limited thereto. For example, the xenon tube may be used as the observation light source. In this case, the observation light amount may also be controlled by providing the xenon tube serving as the observation light source with the xenon tube driving circuit 24 and the light amount detection unit 28.

In the exemplary embodiment, the capacitance of the integration capacitor is determined according to the ISO sensitivity, but the invention is not limited thereto. For example, the capacitance of the integration capacitor may be determined according to an imaging mode such as a spontaneous fluorescent imaging mode or a color imaging mode. For example, since the color imaging mode does not require a large imaging light amount compared to the spontaneous fluorescent imaging mode when selecting the color imaging mode, the capacitance of the integration capacitor may be set to a smaller value compared to the integration capacitor of the spontaneous fluorescent imaging mode. In this way, even in the color imaging mode, the output of the integration circuit is hardly affected by noise or the like compared to the case where the value of the integration capacitor is not changed.

In the exemplary embodiment, various processes are performed by using the CPU 29, but the invention is not limited thereto. Any device which can achieve the above-described function may be used. For example, a field programmable gate array (FPGA) may be used instead of the CPU.

In the exemplary embodiment, the capacitance ratio of each integration capacitor is set to 4, but the invention is not limited thereto.

In the exemplary embodiment, only one of the integration capacitors 40, 41, and 42 is used as the integration capacitor, but the invention is not limited thereto. For example, when the integration capacitor is saturated in the imaging operation requiring a large light amount, the switch 44 is turned on so as to use all of the integration capacitors 40, 41, and 42 to increase the integral capacitance. The integration capacitors 41 and 42 may also be used together, and the integration capacitors 40 and 42 may also be used together.

When the output of the integration circuit 48 for the necessary light emission amount exceeds the upper limit value of the reference voltage, the analog switch 49 may be turned on so as to perform the integration a plurality of times. Specifically, the number of times of integration is obtained by dividing the D/A value corresponding to the necessary light emission amount by the D/A value corresponding to the upper limit value of the reference voltage output from the D/A converter 47. For example, when the division result is 2, the analog switch 49 is turned on so as to reset the output of the integration circuit 48 at the time point when the output of the integration circuit 48 exceeds the reference voltage. Then, the analog switch 49 is turned off again so as to integrate the light emission amount again. The light emission of the xenon tube 3 is stopped at the time point when the output of the integration circuit 48 exceeds the reference voltage again. In this way, the light emission amount may be controlled even when the output of the integration circuit 48 with respect to the necessary light emission amount exceeds the upper limit value of the reference voltage.

Other Embodiments

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-167051 filed Jul. 29, 2011, which is hereby incorporated by reference herein in its entirety.

What is claimed is:

1. An ophthalmologic apparatus comprising:
an integration unit which integrates a light emission amount of a light source illuminating a target eye;
an integral capacitance changing unit which changes a value of an integral capacitance of the integration unit according to the light emission amount necessary for imaging the target eye;
a comparison unit which compares a reference value with an integration value integrated by the integration unit using the value of the integral capacitance changed by the integral capacitance changing unit; and
a light emission control unit which stops the light emission of the light source when the integration value exceeds the reference value as a result of the comparison by the comparison unit,
wherein the integral capacitance changing unit changes the value of the integral capacitance from a value that is larger than zero to another value that is larger than zero.

2. The ophthalmologic apparatus according to claim 1,
wherein the integration unit is provided with a plurality of selectable integral capacitances having different values, and
wherein the integral capacitance changing unit changes the value of the integral capacitance by selecting one integral capacitance from the plurality of integral capacitances.

3. The ophthalmologic apparatus according to claim 2, wherein the values of the plurality of integral capacitances are determined based on the number of the plurality of the integral capacitances and a light amount adjustment range in which the light emission amount of the light source is adjusted.

4. The ophthalmologic apparatus according to claim 1, wherein the reference value is determined according to the value of the integral capacitance changed by the integral capacitance changing unit.

5. The ophthalmologic apparatus according to claim 1, wherein the integral capacitance changing unit changes the value of the integral capacitance to a smaller value as the light emission amount necessary for imaging the target eye decreases.

6. The ophthalmologic apparatus according to claim 1,
wherein the integration unit includes a photo diode which generates a current according to the light emission amount of the light source, and
wherein the photo diode is provided on the optical axis of the light source in a direction opposite to a direction directed from the light source toward the target eye.

7. The ophthalmologic apparatus according to claim 1,
wherein the integration unit includes a photodiode configured to generate a current according to a light emission amount of the light source and an amplifier,
wherein the integral capacitance is connected between input and output of the amplifier, and
wherein the integral capacitance is charged by output of the photodiode.

8. The ophthalmologic apparatus according to claim 2,
wherein the integration unit includes an amplifier,
wherein the plurality of integral capacitances is connected between input and output of the amplifier via a plurality of switches respectively, and
wherein the integral capacitance changing unit is configured to select one of the integral capacitances by controlling the switch.

9. The ophthalmologic apparatus according to claim 8, wherein the plurality of integral capacitances is connected in parallel to each other via the plurality of switches.

10. The ophthalmologic apparatus according to claim 1,
wherein the ophthalmologic apparatus includes a plurality of modes for capturing an image of the target eye, and
wherein a light emission amount necessary for capturing the image of the target eye differs among the modes.

11. The ophthalmologic apparatus according to claim 10, further comprising:
a selection unit configured to select one of the modes,
wherein the integral capacitance changing unit is configured to change the value of the integral capacitance according to the light emission amount necessary for capturing the image of the target eye in a mode selected by the selection unit.

12. The ophthalmologic apparatus according to claim 1, further comprising:
a resetting unit configured to reset the integration value based on a result of comparison of a first integration value indicating the light emission amount of the light source integrated by the integration unit with a first reference value, wherein comparison unit is configured to compare a second integration value indicating the light emission amount of the light source integrated by the integration unit after the integration value is reset by the resetting unit with a second reference value, and wherein the light emission control unit is configured to stop light emission of the light source when the second integration value exceeds the second reference value as a result of comparison of the second integration value with the second reference value.

13. An ophthalmologic method comprising:
integrating a light emission amount of a light source illuminating an target eye;
changing a value of an integral capacitance of the integration unit according to the light emission amount necessary for imaging the target eye;
comparing a reference value with an integration value integrated by the integration unit using the changed value of the integral capacitance; and
stopping the light emission of the light source when the integration value exceeds the reference value as a result of the comparison,
wherein the value of the integral capacitance is changed from a value that is larger than zero to another value that is larger than zero.

14. A non-transitory computer readable storage medium having program code to perform an ophthalmologic method comprising:
integrating a light emission amount of a light source illuminating a target eye;
changing a value of an integral capacitance of the integration unit according to the light emission amount necessary for imaging the target eye;
comparing a reference value with an integration value integrated by the integration unit using the changed value of the integral capacitance; and
stopping the light emission of the light source when the integration value exceeds the reference value as a result of the comparison,
wherein the value of the integral capacitance is changed from a value that is larger than zero to another value that is larger than zero.

15. An ophthalmologic apparatus comprising:
an integration unit which integrates a light emission amount of a light source illuminating an target eye;
an integral capacitance changing unit which changes a value of an integral capacitance of the integration unit according to the light emission amount necessary for imaging the target eye;
a comparison unit which compares a reference value with an integration value integrated by the integration unit using the value of the integral capacitance changed by the integral capacitance changing unit; and
a light emission control unit which controls the light emission of the light source based on a result of comparison by the comparison unit,
wherein the integral capacitance changing unit changes the value of the integral capacitance from a value that is larger than zero to another value that is larger than zero.

16. The ophthalmologic apparatus according to claim 15, wherein the light emission control unit is configured to decrease the light emission amount of the light source based on the result of comparison by the comparison unit.

17. An ophthalmologic method comprising:
integrating a light emission amount of a light source illuminating an target eye;
changing a value of an integral capacitance according to the light emission amount necessary for imaging the target eye;
comparing a reference value with an integration value using the changed value of the integral capacitance; and
controlling the light emission of the light source based on a result of comparison,
wherein the value of the integral capacitance is changed from a value that is larger than zero to another value that is larger than zero.

18. A non-transitory computer readable storage medium having program code to perform an ophthalmologic method comprising:
integrating a light emission amount of a light source illuminating an target eye;
changing a value of an integral capacitance according to the light emission amount necessary for imaging the target eye;
comparing a reference value with an integration value using the changed value of the integral capacitance; and
controlling the light emission of the light source based on a result of comparison,
wherein the value of the integral capacitance is changed from a value that is larger than zero to another value that is larger than zero.

19. The ophthalmologic apparatus according to claim 1, wherein the integral capacitance changing unit is configured to change the value of the integral capacitance to a smaller value as the light emission amount necessary for imaging the target eye is smaller.

20. The ophthalmologic apparatus according to claim 15, wherein the integral capacitance changing unit is configured to change the value of the integral capacitance to a smaller value as the light emission amount necessary for imaging the target eye is smaller.

* * * * *